United States Patent [19]

Wegman

[11]  4,447,648

[45]  May 8, 1984

[54] PROCESS FOR MAKING ALDEHYDES FROM KETALS

[75] Inventor: Richard W. Wegman, Cross Lanes, W. Va.

[73] Assignee: Union Carbide Corporation, Danbury, Conn.

[21] Appl. No.: 413,466

[22] Filed: Aug. 31, 1982

[51] Int. Cl.$^3$ .............................................. C07C 45/49
[52] U.S. Cl. ................................... 568/484; 568/451; 568/478
[58] Field of Search ................ 568/478, 485, 454, 451

[56] References Cited

U.S. PATENT DOCUMENTS

| | | | |
|---|---|---|---|
| 2,429,875 | 10/1947 | Good | 585/252 |
| 2,555,950 | 6/1951 | Wilson | 568/902 |
| 2,759,979 | 8/1956 | Hagemeyer et al. | 568/485 |
| 3,356,734 | 12/1967 | Kuraishi et al. | 568/487 |
| 3,928,459 | 12/1975 | Mercier | 568/485 |
| 4,062,898 | 12/1977 | Dubeck | 568/909 |
| 4,201,868 | 5/1980 | Slinkard | 560/232 |

OTHER PUBLICATIONS

Organic Synthesis via Metal Carbonyl, pp. 1,26,28,30 and 32, (1976), vol. 2.

Primary Examiner—Werren B. Lone
Attorney, Agent, or Firm—Bernard Francis Crowe

[57] ABSTRACT

Saturated aliphatic aldehydes are prepared by contacting acetals or ketals with synthesis gas and a Group VIII compound, preferably a cobalt compound.

21 Claims, No Drawings

PROCESS FOR MAKING ALDEHYDES FROM KETALS

BACKGROUND OF THE INVENTION

This invention pertains to a process for making saturated aliphatic aldehydes from ketals and particularly to the reaction of acetals or ketals with synthesis gas in the presence of a cobalt catalyst.

Much research work has been done on the conversion of synthesis gas, that is, mixtures of carbon monoxide and hydrogen, into low molecular weight organic compounds. For example, methanol has been made from synthesis gas and then further reacted with synthesis gas by hydroformylation, homologation, or carbonylation to provide acetaldehyde, ethanol and acetic acid, respectively. These reactions are catalyzed by one or more transition metals of Group VIII of the Periodic Table. In these reactions a halogen, as for example, iodine, or halogen containing compounds, for example, methyl iodide, must be utilized in conjunction with the metal catalyst in order for a reaction to be carried out at commercially acceptable rates and selectivities.

It is therefor an object of this invention to provide a process which utilizes synthesis gas and produces linear aldehydes at high conversion rates and selectivities under relatively mild reaction conditions.

It is another object of this invention to provide a process for producing linear aldehydes via synthesis gas with a minimum of loss of the starting materials, that is, with high conversions of starting materials to the desired aldehydes.

Other objects will become apparent to those skilled in the art upon a reading of the specifications.

BACKGROUND ART

A general review of the work done on homologation/hydroformylation reactions of acetals is given in Organic Synthesis via Metal Carbonyls, Wiley-Interscience, 1976. Pino et. al. (Chem Ind. 1960, 1240) reported the reaction of an orthoester, R—C(OR)$_3$, with synthesis gas and a cobalt catalyst resulting in the formation of a linear aldehyde, alcohol, and ester. In contrast, the reaction of an acetal, R—C(OR)$_2$H, with synthesis gas has been reported to result in the formation of glycol ethers or 2-methoxy aldehydes. For instance, U.S. Pat. No. 2,555,950, (DuPont) claimed a process for the production of 2-methoxy aldehydes and 2-methoxy alkanols from the reaction of synthesis gas with acetals derived from 2 to 3 carbon alkanols. The reaction was carried out at high temperatures (150°–250° C.) and pressures (12,000–22,500 psi) and was catalyzed by cobalt. Only acetals were claimed and the methoxy substituted aldehydes/alcohols were the sole product. Similar chemistry was observed for the reaction of formyls with synthesis gas.

In U.S. Pat. No. 2,429,875 (DuPont), glycol ethers were produced via the reaction of formyls with synthesis gas. The reaction was carried out at high temperatures (100°–350° C.) and pressures (9000–15,000 psi) and was catalyzed by a metal from Group VIII of the Periodic Table.

More recently, U.S. Pat. No. 4,062,898 (Ethyl Corporation) claimed a process for the production of linear alcohols by a reaction of acetals (particularly methylal) with synthesis gas. The process was carried out at 150°–250° C. and 500–5,000 psi with a cobalt-ruthenium-iodine catalyst. Little, if any, formation of linear aldehydes were observed in this reaction. Ketals were claimed as a feedstock.

DISCLOSURE OF THE INVENTION

A method of preparing saturated aliphatic aldehydes has now been discovered which comprises contacting a gem diether having the formula:

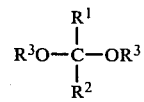

wherein each of R$^1$ and R$^2$ is a monovalent radical selected from the class consisting of alkyl radicals having 1 to about 15 carbons, aryl radicals having 6 to about 10 carbons and cycloalkyl radicals having 5 to about 7 carbons;

R$^3$ is a monovalent radical selected from the group consisting of alkyls having 1 to about 10 carbons, aryls having 6 to about 10 carbons, and cycloalkyl radicals having 5 to about 7 carbons with a catalytic amount of a Group VIII compound at a temperature of about 80° C. to about 175° C. and a pressure of about 500 to about 6,000 psig in the presence of a mixture of carbon monoxide and hydrogen.

The term "catalytic amount of Group VIII compound" is defined to mean one where the mole ratio of Group VIII metal to gem diether is about 1:5 to about 1:50,000. The preferred amount is a mole ratio of Group VIII metal to gem diether of about 1:50 to about 1:500. The preferred Group VIII metal is cobalt.

While the preferred Group VIII metal used in the catalysts of this invention is cobalt, the other members can be used too, viz., iron, nickel, ruthenium, rhodium, osmium, iridium or platinum.

The gem diethers of this invention are ketals depending upon the nature of R$^1$, R$^2$, and R$^3$.

The ketals used in this invention can be derived from a typical saturated aliphatic ketone with straight or branched alkyl chains having 1 to about 15 carbon atoms. The ketals can be aromatic or have one position with an aromatic ring and another with an alkyl chain. Exemplary dialkyl ketones include acetone, methylethylketone, diethylketone, dibutylketone, dipentylketone, and other branched alkyl ketones having up to about 5 carbon atoms. Exemplary aromatic ketones include diphenylketone, alkyl substituted diphenylketones, and mixed aromatic-alkyl ketones, such as benzophenone. The most preferred ketone is 2,2-dimethoxypropane.

The alcohol moieties of both the ketals used in this invention can be derived from saturated aliphatic alcohols either straight or branched having 1 to about 10 carbons, and preferably 1 to about 3 carbons and also aromatic or alkyl substituted aromatic alcohols such as phenol, anisole and the like. The most preferred alcohols are methanol and ethanol.

While the catalyst for the invention consists of a Group VIII transition metal, preferably cobalt, optionally a Co-Halide-ER$_3$ catalyst, wherein Co is the cobalt containing compound, Halide is the halogen containing compound and ER$_3$ is a Group V trivalent ligand where R is an organic moiety, can be utilized.

The cobalt component of the catalyst system can be supplied from any number of sources, many of which are known to those of ordinary skill in the art. Thus, it is not necessary for an understanding thereof to specifically enumerate every suitable type and specific compound since any of the known compounds can be used. Nevertheless, descriptive of some of the useful cobalt sources are the known cobalt carboxylates such as cobalt formate, cobalt acetate, cobalt benzoate, cobalt toluate, cobalt propionate, cobalt butyrate, cobalt valerate, cobalt hexanoate, cobalt cyclohexanebutyrate, and the like; the cobalt carbonyls such as dicobalt octacarbonyl, acetyl cobalt tetracarbonyl, tricobalt dodecacarbonyl, and the like, including their phosphine substituted analogs many of which are known to those skilled in the art; the cobalt oxides such as cobalt oxide; cobalt hydroxide; cobalt carbonate; and cobalt bicarbonate. When a phosphorus substituted analog or a cobalt halide is used, proper adjustment is required to maintain the ratios as they are defined in this invention.

The cobalt concentration in the reaction can be varied from about 1 to about 40 mgm-atoms per mole of alcohol used; preferably from about 2 to about 20 mgm-atoms per mole of alcohol and most preferably from about 3 to about 15 mgm-atoms per mole of alcohol.

The halide component of the catalyst can be a halogen compound containing iodine, bromine or chlorine or two or more of the same, or the elemental halogen per se, or any mixtures of compounds and/or elements. The preferred halogen compound is iodine or inorganic or organic compounds containing the iodine atom. The suitable halogen compounds are well known to those of average skill in this art and a complete listing is not necessary for their comprehension. Illustrative thereof one can mention barium iodide, hydriodic acid, cobalt iodide, potassium iodide, lithium iodide, sodium iodide, calcium iodide, ammonium iodide, methyl iodide, ethyl iodide, propyl iodide, 2-ethylhexyl iodide, n-decyl iodide, acetyl iodide, propionyl iodide; the organic ammonium iodides of the formula $R'_4NI$ and the organic phosphonium iodides of the formula $R'_4PI$ in which $R'$ is alkyl, saturated or unsaturated, substituted or unsubstituted, having from 1 to about 10 carbon atoms or aryl, unsubstituted or substituted, having from 6 to 10 ring carbon atoms such as trimethyl ammonium iodide, tetraethyl ammonium iodide, tetra-2-ethylhexyl ammonium iodide, tetraphenyl ammonium iodide, tetramethyl phosphonium iodide, tetrapropylphosphonium iodide, tetra-2-ethylhexyl phosphonium iodide, tetraphopyl phorphonium iodide, tetra-2-ethylhexyl phorphonium iodide, methyltriphenyul phosphonium iodide, and the like; methylammonium iodide, triphenylammonium iodide, tricyclohexylammonium iodide, tri-p-tolyl-ammonium iodide, decylammonium iodide, ethylphosphonium iodide, triphenylphosphonium iodide, tricylcohexylphosphonium iodide, tri-p-tolyphosphonium iodide, and the like; also useful are bromine and its corresponding compounds and chlorine and its corresponding compounds. Any source of halogen atom can be used provided that it does not have a deleterious effect on the reaction. Again, one must maintain the defined ratios.

The amount of halogen charged is dependent upon the amount of cobalt employed. The halogen:cobalt mgm-atom ratio is at least 0.5:1 and can be as high as 20:1. it is preferably from about 1:1 to about 10:1 and most preferably from about 2:1 to about 5:1.

Another component of the optional catalyst is a Group V trivalent ligand, $ER_3$, where $E=N,P,As,O,Sb$ and R is an organic moiety. The preferred $ER_3$ representatives are $NR_3$ and $PR_3$.

The phosphorus component of the catalyst is a trivalent phosphorus compound such as the simple trivalent phosphorus compounds of the formulas $PR_3$ or $P(OR)_3$ or $RP(OR)_2$ or $R_2POR$ or the polydentate trivalent phosphines of the formula $R_2PC_nH_{2n}PR_2$, or mixtures thereof, in which R is an alkyl group, saturated or unsaturated, linear or branched, having from 1 to 20 or more carbon atoms, preferably from 4 to 10 carbon atoms; or an aryl, alkaryl or aralkyl group having from 6 to 10 ring carbon atoms, preferably 6 ring carbon atoms; or cycloalkyl having from 5 to 8 ring carbon atoms, preferably 5 or 6 ring carbon atoms; and n is an integer having a value of from 2 to 8 preferably 2 to 4. The R groups may be the same or different in the molecule and they can be unsubstituted or substituted with groups which will not unduly interfere with the reaction or have a deleterious effect on it. Mixtures of the phosphorus compounds can be used if one so desires. Though those skilled in the art know the phosphorus compounds, illustrative of suitable compounds one can mention triethylphosphine, tributylphosphine, tri-2-ethylhexylphosphine, triphenylphosphine, tri(4-methoxyphenyl)phosphine, tri-p-tolylphosphine, tri(3-chlorophenyl)phosphine, diphenyl hexylphosphine, dimethyl (3-methoxyphenyl)phosphine, dibutylstearylphosphine, tribenzylphosphine, tricyclohexyphosphine, cyclohexyl dibutylphosphine, propyl diphenylphosphine, dipropyl phenylphosphine, ethyl diproxyphosphine, phenyl diethylphosphine, triethylphosphite, tributylphosphite, tridecylphosphite, trioctadecylphosphite, triphenylphosphite, tribenzylphosphite, tricyclo- hexylphosphite, diethylphenylphosphite, methyl diethoxyphosphine, ethyl diethoxyphosphine, butyl dibutoxyphosphine, ethyl dihenoxyphosphine, phenyl diethoxyphosphine, tolyl diethoxyphosphine, diethyl ethoxyphosphine, dibutyl butoxyphosphine, cyclohexyl diethyoxyphosphine, diethyl cyclohexoxyphosphine, diethyl phenoxyphosphine, bis(diphenylphosphino)-ethane, bis-(diethylphosphino)-propane, bis-(diphenylphosphino)-butane, bis-(diethylphosphino)-octane, and the like.

The trivalent nitrogen compound of the catalyst is an amine of the formula $NR_3$ or an amide of the formula $R''CONR_2''$ in which R is as previously defined and $R''$ is hydrogen or alkyl, saturated or unsaturated, unsubstituted or substituted having from 1 to about 20 carbon atoms, preferably from 4 to 10 carbon atoms, cycloalkyl, substituted or unsubstituted, having from 5 to 8 ring carbon atoms, or aryl, substituted or unsubstituted, having from 6 to 10 ring carbon atoms. Illustrative thereof are trimethylamine, triethylamine, tri-n-butylamine, tri-t-butylamine, tri-2-ethylhexylamine, methyl dibutylamine, tridodecylamine, tristearylamine, ethyl dibutylamine, tricyclohexylamine, triphenylamine, tri(4-methoxyphenyl)amine, tri(p-chlorophenyl)-amine, dibutyl phenylamine, dipentyl cyclopentylamine, ethyl diphenylamine, trinaphthylamine, tri-p-toylamine, tribenzylamine, tri(3-methylcyclohexyl)amine, formamide, acetamide, chloroacetamide, propionamide, benzamide, butylamide, N-methyl formamide, N-methylacetamide, N,N-dimethyl propionamide, N,N-dihexyl butylamide, N,N-dihexyl acetamide, 2-methyl hexylamide, N,N-isobutyl propionamide, N,N-dodecyl nonamide, and the like.

The molar ratio of $ER_3$ to Co can vary over a wide range. The preferred range is 50:1 to 1:50 and the most preferred is 10:1 to 1:10.

Although temperatures in the range of about 80°–175° C. can be used in the practice of this invention, it is preferred to use a range of about 120°–160° C.

Pressures of about 500 to about 6,000 psig can be used in the practice of this invention but it is preferred to use a range of about 2,000 to about 4,000 psig.

The ratio of carbon monoxide to hydrogen in the synthesis gas used in this invention can range from about 5:1 to about 1:5 but preferably is in the range of about 2:1 to about 1:2.

Although the claimed method does not require a solvent, one can be used if desired. Exemplary solvents include alkanes having about 5 to about 12 carbons, such as, pentane, hexane, heptane, octane, and the like; saturated aliphatic alcohols having 1 to about 8 carbons, such as methanol, ethanol, propanol, butanol, octanol, and the like; alkyl glycol ethers having 4 to about 12 carbons, such as, dimethyl glycol ether, diethyl glycol ether, dimethyl diethylene glycol ether, diethyl diethylene glycol ether, and the like; diaryl ethers having 12 to about 18 carbons, such as diphenyl ether, ditolyl ether, and the like.

This invention provides a process that consumes only alcohol in the formation of aldehyde. The by-products of the reaction are recycled back:

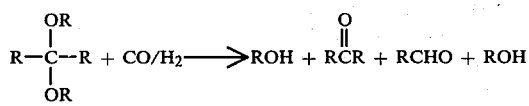

The recycle is carried out by removing the product aldehyde, RCHO and replenishing the consumed alcohol, ROH. The formation of the ketal by the reaction of aldehyde or ketone with excess alcohol is known. Thus the net reaction is the conversion of alcohol into aldehyde. Regeneration of ketal can be effected in two modes:

(1) A two-step process where by-products alcohol and ketone are removed from the reactor and combined with additional alcohol in a separate stage.

(2) A one-step, in situ formation of the ketal by feeding additional alcohol directly into the reactor. In this case aldehyde and water are removed from the reactor.

The aldehydes prepared in the practice of this invention are of high enough purity to be used in their conventional role as chemical intermediates, such as, condensation reactions, reduction to alcohols, oxidation to acids, and the like.

The invention is further described in the example which follow. All parts and percentages are by weight unless otherwise specified.

GENERAL EXPERIMENTAL PROCEDURE

A general procedure as exemplified by the reaction of 2,2-dimethoxypropane is as follows. Prior to charging the reactants (catalyst, diluent, and methanol) the autoclave was washed with methanol at 100° C. at a pressure of 500–1,000 psig synthesis gas (CO:H$_2$::1:1) for 30 minutes. The reactor was drained, opened, rinsed with acetone, and dried with nitrogen. To the opened and cleaned reactor was charged first the liquid and then the solid reactants. The reactor was closed, purged with synthesis gas, and then pressured to 1,000 psig with synthesis gas. With agitation (750 rpm), the reactor contents were heated to the prescribed temperature, usually between 120°–150° C. in about 45 minutes. As soon as the temperature had been reached, the reactor was brought to the desired pressure plus 250 psig. The reaction was allowed to consume gas until the pressure had fallen to 250 psig below the desired pressure. The reaction was then repressured. One such cycle was considered 500 psig gas uptake. Unless otherwise specified, reactions were allowed to proceed until 3000 psig gas uptake had occurred.

At the end of an experiment, the reactor contents were normally cooled to 10° C. A vapor phase sample was taken and analyzed for carbon monoxide, hydrogen, carbon dioxide, and methane plus other gaseous hydrocarbons by means of vapor phase chromatography.

The reactor gas phase was vented through two dry ice acetone traps and then a 2.5 gallon saturated solution of calcium hypochloride to remove iron and/or nickel carbonyls. The reactor was pressurized three times with 90 psig nitrogen and vented through the same trap-vent system.

The reactor contents were dumped into a chilled pressure bottle and crown capped. A Hewlett-Packard Model 5880 gas chromatograph was employed with two columns ⅛"×10' Chromosorb 101 60/80 mesh which were connected in series with a ⅛" union tube.

EXAMPLE 1

Cobalt Acetate Catalyzed Preparation of Acetaldehyde

Into a 300 cc autoclave were charged 24 millimoles of Co(OCOCH$_3$)$_2$.4H$_2$O(5.97 g) and 1.22 moles of 2,2-dimethoxypropane (127.05 g.). Following the procedures described above, the reactor was heated to 135° C. and the pressure was adjusted to 2250 psig. The ratio of hydrogen to carbon monoxide was 1.5. The reaction commenced upon pressuring the vessel to 2250 psig as evidenced by a constant uptake of synthesis gas. The reaction proceeded for approximately 30 minutes after which the reactor was cooled and the product analyzed. Thus the reaction conditions utilized were:

| | |
|---|---|
| Co(OCOCH$_3$).4 H$_2$O | = 24 millimoles |
| 2,2-dimethoxypropane | = 1.22 moles |
| Temperature, °C. | = 135 |
| Pressure, psig | = 2250 |
| H$_2$/CO | = 1.5 |

The products obtained and their approximate molar amounts are given below:

| PRODUCT | MOLES |
|---|---|
| Methanol | 0.9 |
| Acetone | 0.6 |
| Acetaldehyde* | 0.3 |
| 4-methyl-2-pentanone | 0.1 |
| Water | 0.07 |
| Methane | 0.03 |
| Dimethylether | Trace |

*Includes acetaldehyde equivalent in dimethyl acetal

The remainder of the product mixture was unreacted 2,2-dimethoxypropane. Under the reaction conditions utilized the rate to acetaldehyde was 4.8 gram moles/l-hr.

EXAMPLE 2

Example 1 was repeated with the exception that the following conditions and amounts were used:

| | |
|---|---|
| Co(OCOCH$_3$)$_2$.4 H$_2$O | = 12 millimoles (2.98 grams) |
| 2,2-dimethoxypropane | = 0.609 moles (63.5 grams) |
| Diethyl Carbitol | = 75 ml |
| Temperature, 0° C. | = 140 |
| Pressure | = 250 psig |

The product distribution was similar to that obtained in Example 1. Under the conditions utilized in this Example, the rate of conversion to acetaldehyde was 3.3 gram moles/1-hr.

Note that a solvent was used in this case, viz., diethyl CARBITOL. The cobalt concentration was half that used in Example 1. The solvent/dimethoxypropane ratio was 50:50 by volume.

The rate of conversion to acetaldehyde was slightly lower than that obtained in Example 1 which is ascribed to the reactant/catalyst dilution.

EXAMPLES 3-5

Using the same reaction conditions outlined in Example 1, the invention was practiced in a variety of solvents. The results obtained in terms of conversion rate to acetaldehyde are dilineated below:

| SOLVENT | ACETALDEHYDE RATE (g mole/l hr) |
|---|---|
| Methanol | 1.0 |
| Diphenylether | 0.5 |
| Octane | 0.2[a] |

[a]In the case of octane the temperature was 150° C. and the pressure was 3500 psig.

The product distribution in all three examples was similar to that obtained in example 1.

It may be noted that of the solvents compared here the alkane, octane, gave lower reaction rates.

Methanol served as a good solvent. However, an additional by-product, methyl acetate, was observed when it was used.

EXAMPLES 6-8

The procedure and conditions described in Example 1 were repeated with the exception that methanol was used as the solvent at varying pressures and temperatures. The results obtained are delineated below:

| Example | Temp. °C. | Pressure, psig | Acetaldehyde Rate (gram moles/l/hr) |
|---|---|---|---|
| 6 | 150 | 3500 | 1.9 |
| 7 | 140 | 3500 | 1.0 |
| 8 | 140 | 2500 | 1.0 |

When a solvent is utilized in this invention (50:50 by volume), a temperature of about 140° C. and a pressure of at least 2500 psig are required in order for the reaction to proceed at a reasonable rate.

Temperatures above 150° C. and pressures above 4000 psig appear to enhance the formation of heavy condensation products.

EXAMPLES 9-13

Example 1 was repeated with the exception that a halide [iodine (I$_2$)] and triphenyl phosphine (P) were added to the reactants. The results are presented below:

| EXAMPLE | I/Co[a] | P/I$_2$[b] | TEMP °C. | PRESSURE PSIG | ACETALDEHYDE RATE[c] |
|---|---|---|---|---|---|
| 9 | 3.5 | 3.1 | 180 | 2500 | 3.5 |
| 10 | 3.5 | 3.1 | 140 | 2500 | 3.0 |
| 11 | 3.5 | 1.1 | 140 | 3500 | 4.0 |
| 12 | 2.0 | 1.0 | 140 | 3500 | 3.0 |
| 13 | 2.0 | 1.0* | 140 | 3500 | 4.4 |

[a]Ratio of iodine to cobalt
[b]Ratio of triphenyl phosphine to iodine
[c]Rate of formation of acetaldehyde in gram moles/liter of solution/hour.
*Triphenyl phosphine oxide used in place of triphenyl phosphine.

The cobalt concentration in the above runs was 5.33 times 10$^{-2}$ M.

The methanol/dimethoxypropane ratio was 50:50 in volume.

It is apparent from the above data that high rates to acetaldehyde can be achieved when iodine and triphenylphosphine are used. This is more significant when it is taken into account that a solvent was used in each run. Thus, two advantages appear to be obtained when a halogen and a phosphine are added to the reactants, viz., high rates when solvent is present and marked decrease in formation of heavy condensation products. The principal effect is on the suppression of formation of 4-methyl-2-pentanone to less than 1% of the observed product weight. Thus the selectivity to acetaldehyde is higher when a halide/phosphine combination is utilized.

EXAMPLE 14

The procedure and equipment described in Example 1 was used with the following changes: 1,1-dimethoxycyclohexane; 56.9 g, 0.4 moles; CoI$_2$ 1.56 g, 5 millimoles; Co(OAc)$_2$.4 H$_2$O, 1.25 g, 5 millimoles; tributylamine, 0.93 g, 12 millimoles.

A temperature of 135° C. and a pressure of 2500 psig for 60 minutes afforded the following products:

| PRODUCT | MOLES |
|---|---|
| Acetaldehyde | 0.12 |
| Methanol | 0.28 |
| Cyclohexanone | 0.18 |

I claim:
1. Method of preparing saturated aliphatic aldehydes which comprises contacting a gem diether having the formula:

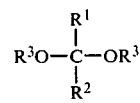

wherein
each of R$^1$ and R$^2$ is a monovalent radical selected from the class consisting of alkyl, aryl radicals having 6 to about 10 carbon and cycloalkyl radicals having 5 to about 7 carbons;
R$^3$ is a monovalent radical selected from the group consisting of alkyls having 1 to about 10 carbons and aryl having 6 to about 10 carbons with a catalytic amount of a Group VIII compound at a temperature of about 80° to 175° C. and a pressure of about 500 to about 6000 psig in the presence of a mixture of carbon monoxide and hydrogen.

2. Method claimed in claim 1 wherein $R^1$, $R^2$ and $R^3$ are each methyl.

3. Method claimed in claim 1 wherein the temperature is about 120° C. to about 160° C.

4. Method claimed in claim 1 wherein the pressure is about 2000 to about 4000 psig.

5. Method claimed in claim 1 wherein the ratio of carbon monoxide to hydrogen ranges from about 2:1 to about 1:2.

6. Method claimed in claim 1 wherein the mole ratio of Group VIII metal to gem diether in the Group VIII compound ranges from about 1:5 to about 1:50000.

7. Method claimed in claim 1 wherein the mole ratio of Group VIII metal to gem diether in the Group VIII compound ranges from about 1:50 to about 1:500.

8. Method claimed in claim 1 wherein the Group VIII compound is a cobalt compound.

9. Method claimed in claim 8 wherein the cobalt compound is a cobalt salt of a saturated aliphatic carboxylic acid having 1 to about 20 carbons.

10. Method claimed in claim 9 wherein the carboxylic acid is acetic acid.

11. Method claimed in claim 8 wherein the cobalt compound is a cobalt oxide.

12. Method claimed in claim 1 wherein the cobalt compound is a cobalt carbonyl.

13. Method claimed in claim 12 wherein the cobalt carbonyl is dicobalt octacarbonyl.

14. Method claimed in claim 1 wherein the gem diether is dissolved in an inert solvent.

15. Method claimed in claim 14 wherein the inert solvent is a saturated aliphatic alcohol.

16. Method claimed in claim 15 wherein the alcohol is methanol.

17. Method claimed in claim 14 wherein the inert solvent is a gylcol alkyl ether.

18. Method claimed in claim 17 wherein the ether is diethylene glycol diethyl ether.

19. Method claimed in claim 8 wherein the cobalt compound is supplemented by a mixture of a halogen and triphenyl phosphine wherein the molar ratio of cobalt to triphenyl phosphine is in the range of about 1:50 to about 50:1 and the halogen:cobalt milligram atom ratio is about 0.5:1 to about 20:1.

20. Method claimed in claim 19 wherein the halogen is iodine.

21. Method of preparing saturated aliphatic aldehydes claimed in claim 1 wherein the gem diether is 2,2-dimethoxy propane.

* * * * *